United States Patent
Glik et al.

(10) Patent No.: US 11,617,504 B2
(45) Date of Patent: Apr. 4, 2023

(54) RETINAL CAMERA WITH DYNAMIC ILLUMINATOR FOR EXPANDING EYEBOX

(71) Applicant: Verily Life Sciences LLC, South San Francisco, CA (US)

(72) Inventors: Eliezer Glik, San Francisco, CA (US); Sam Kavusi, Menlo Park, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 285 days.

(21) Appl. No.: 16/943,879

(22) Filed: Jul. 30, 2020

(65) Prior Publication Data

US 2021/0076926 A1 Mar. 18, 2021

Related U.S. Application Data

(60) Provisional application No. 62/902,286, filed on Sep. 18, 2019.

(51) Int. Cl.
*A61B 3/00* (2006.01)
*A61B 3/12* (2006.01)
*A61B 3/14* (2006.01)

(52) U.S. Cl.
CPC ............ *A61B 3/0008* (2013.01); *A61B 3/12* (2013.01); *A61B 3/14* (2013.01)

(58) Field of Classification Search
CPC ............ A61B 3/0008; A61B 3/12; A61B 3/14
USPC .................................................. 351/206
See application file for complete search history.

(56) References Cited

U.S. PATENT DOCUMENTS

| | | | |
|---|---|---|---|
| 4,834,528 A | 5/1989 | Howland et al. |
| 5,585,873 A | 12/1996 | Shalon et al. |
| 6,733,129 B2 | 5/2004 | Masaki |
| 7,458,685 B2 | 12/2008 | Liang et al. |
| 7,499,634 B2 | 3/2009 | Yogesan et al. |
| 7,677,730 B2 | 3/2010 | Shimizu |

(Continued)

FOREIGN PATENT DOCUMENTS

JP    2017099717 A    6/2017

OTHER PUBLICATIONS

International Search Report and Written Opinion, dated Nov. 26, 2020, in corresponding International Patent Application No. PCT/US2020/048782, 7 pages.

(Continued)

*Primary Examiner* — Mohammed A Hasan
(74) *Attorney, Agent, or Firm* — Christensen O'Connor Johnson Kindness PLLC (57) ABSTRACT

A dynamic illuminator includes a central aperture, a ring of inner light sources, a plurality of primary illumination arrays, and a plurality of secondary illumination arrays. The ring of inner light sources is arranged around the central aperture. The plurality of primary illumination arrays extends along radial axes from the central aperture outside of the ring of inner light sources, wherein the primary illumination arrays each includes a plurality of primary light sources. The plurality of secondary illumination arrays is disposed along secondary axes extending from the central aperture outside of the ring of inner light sources. The secondary illumination arrays each includes a plurality of secondary light sources. The secondary axes of the secondary illumination arrays are disposed angularly between adjacent ones of the primary illumination arrays.

20 Claims, 7 Drawing Sheets

(56) References Cited

U.S. PATENT DOCUMENTS

| | | | |
|---|---|---|---|
| 7,878,653 | B2 | 2/2011 | Ichikawa et al. |
| 7,954,949 | B2 | 6/2011 | Suzuki |
| 8,408,464 | B2 | 4/2013 | Zhu et al. |
| 8,684,529 | B2 | 4/2014 | Johansson et al. |
| 8,811,657 | B2 | 8/2014 | Feiwes et al. |
| 8,955,971 | B2 | 2/2015 | Ichikawa et al. |
| 8,998,411 | B2 | 4/2015 | Tumlinson et al. |
| 9,125,559 | B2 | 9/2015 | Kersting et al. |
| 9,271,646 | B2 | 3/2016 | Neal et al. |
| 9,289,122 | B2 | 3/2016 | Chinnock et al. |
| 9,743,832 | B2 | 8/2017 | de Paz Sicam et al. |
| 2005/0023356 | A1* | 2/2005 | Wiklof ............... G06K 7/10851 235/462.42 |
| 2013/0010259 | A1 | 1/2013 | Carnevale |
| 2013/0057828 | A1* | 3/2013 | de Smet ................ A61B 3/12 351/207 |
| 2013/0194548 | A1* | 8/2013 | Francis ................ A61B 3/15 351/208 |
| 2013/0208243 | A1 | 8/2013 | Sakagawa |
| 2013/0329189 | A1 | 12/2013 | Mizucchi |
| 2014/0240666 | A1 | 8/2014 | Ootsuki |
| 2016/0174838 | A1 | 6/2016 | Herranen et al. |
| 2016/0302665 | A1 | 10/2016 | Swedish et al. |
| 2016/0317031 | A1 | 11/2016 | Yang et al. |
| 2016/0338589 | A1 | 11/2016 | Carrasco-Zevallos et al. |
| 2018/0055351 | A1* | 3/2018 | Yates ................ A61B 3/0008 |
| 2018/0113419 | A1* | 4/2018 | Stafford ............ G02B 27/0172 |
| 2019/0046031 | A1* | 2/2019 | Kramer ............... A61B 3/0008 |
| 2019/0110677 | A1 | 4/2019 | Walsh et al. |

OTHER PUBLICATIONS

Bengtsson et al., "A New Generation of Algorithms for computerized threshold perimetry, SITA", ACTA Ophthalmologica Scandinavica, 5 pages.

Dehoog et al., "Optimal parameters for retinal illumination and imaging in fundus cameras", Optical Society of America, Dec. 20, 2008, 9 pages.

De Matos et al., "Coaxial Fundus Camera for Ophthalmology", SPIE vol. 9578, 2015, 5 pages.

Fan et al., "Modeling Transient Pupillary Light Reflux Induced by a Short Light Flash", IEEE Transactions on Biomedical Engineering, vol. 58, No. 1., Jan. 2011, 7 pages.

TRC-NW8 Non-Mydriatic Retinal Camera, Topcon Medical Systems, Inc., www/topconmedical.com/products/trcnw8.html, 2016, 1 page.

This is CenterVue International Web Site, http://www/centervue.com, Aug. 31, 2016, 5 pages.

Sugita et al., "Motion artifact and speckle noise reduction in polarization sensitive optical coherence tomography by retinal tracking", Biomedical Optics Express, Dec. 6, 2013, 7 pages.

Swedish et al., "eyeSelfie: Self Directed Eye Alignment using Reciprocal Eye Box Imaging", MIT Media Lab—Camera Culture Group, 2015, 3 pages.

Tran et al., "Construction of an Inexpensive, Hand-Held Fundus Camera through Modification of a Consumer "Point-and-Shoot" Camera", IOVS, Nov. 9, 2012, 10 pages.

Japanese Office Action, dated Jan. 4, 2023, in corresponding Japanese Patent Application No. 2022-502192, 3 pages.

\* cited by examiner

RETINAL CAMERA WITH DYNAMIC ILLUMINATOR FOR EXPANDING EYEBOX

CROSS-REFERENCE TO RELATED APPLICATIONS

This application claims the benefit of U.S. Provisional Application No. 62/902,286, filed Sep. 18, 2019, which is hereby incorporated by reference in its entirety.

TECHNICAL FIELD

This disclosure relates generally to retinal imaging technologies, and in particular but not exclusively, relates to illumination techniques for retinal imaging.

BACKGROUND INFORMATION

Retinal imaging is a part of basic eye exams for screening, field diagnosis, and progress monitoring of many retinal diseases. Conventional retinal cameras typically have a very limited eyebox due to the need to block deleterious image artifacts. The eyebox for a retinal camera is a three-dimensional region in space typically defined relative to an eyepiece of the retinal camera and within which the center of a pupil or cornea of the eye should reside to acquire an acceptable image of the retina. The small size of conventional eyeboxes makes retinal camera alignment difficult.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method of operation of a retinal camera with a dynamic illuminator having an expanded eyebox are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

High fidelity retinal images are important for screening, diagnosing, and monitoring many retinal diseases. To this end, reducing or eliminating instances of image artifacts that occlude or otherwise malign portions of the retinal image is desirable.

Figure 1:
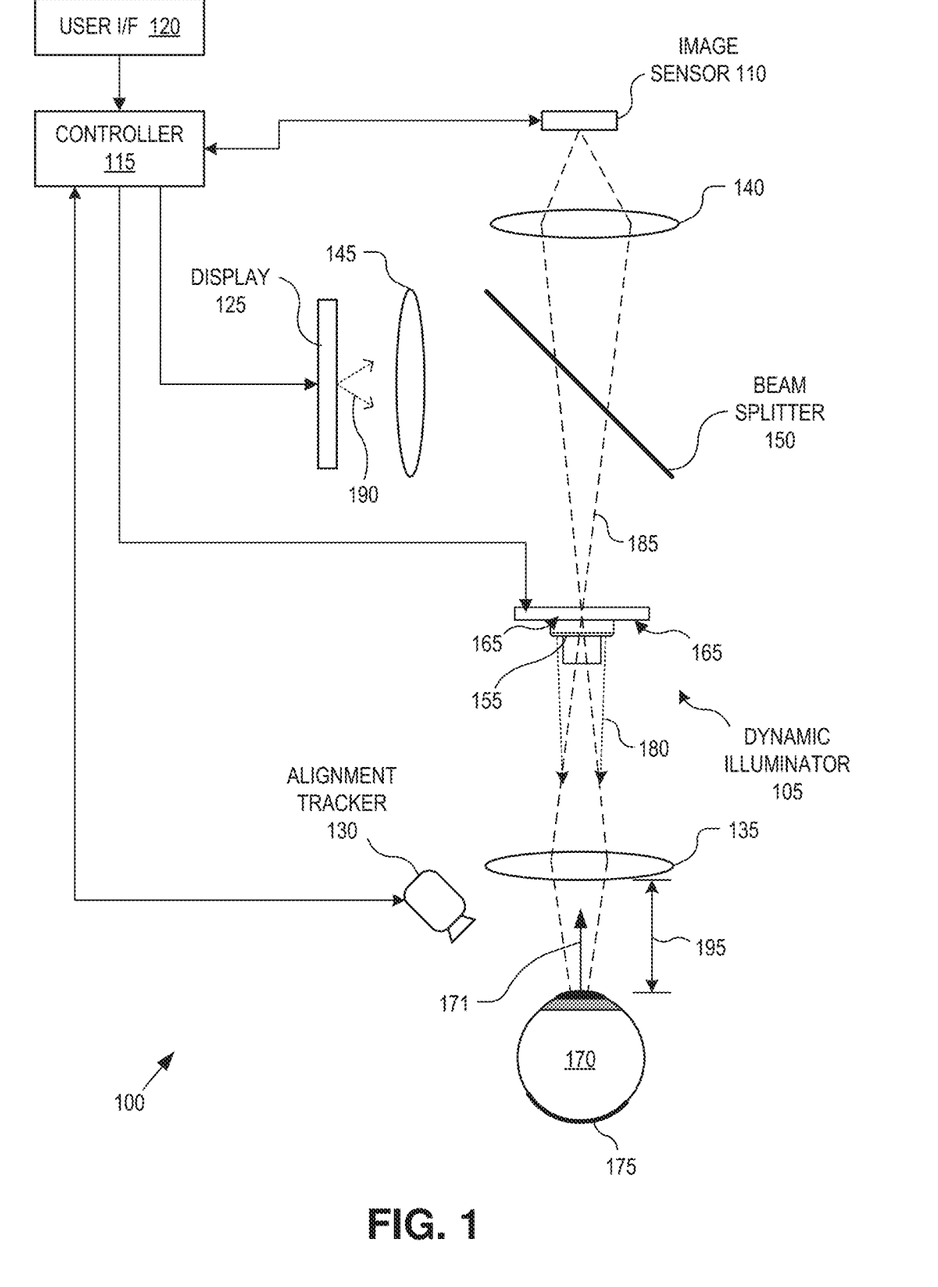
FIG. 1 illustrates a retinal imaging system with a dynamic illuminator, in accordance with an embodiment of the disclosure.

FIG. 1 illustrates a retinal imaging system 100 with a dynamic illuminator, in accordance with an embodiment of the disclosure. The illustrated embodiment of retinal imaging system 100 includes a dynamic illuminator 105, an image sensor 110, a controller 115, a user interface 120, a display 125, an alignment tracker 130, and an optical relay system. The illustrated embodiment of the optical relay system including lenses 135, 140, 145 and a beam splitter 150. The illustrated embodiment of dynamic illuminator 105 includes an inner baffle 155 surrounding a center aperture and illumination arrays 165.

The optical relay system serves to direct (e.g., pass or reflect) illumination light 180 output from dynamic illuminator 105 along an illumination path through the pupil of eye 170 to illuminate retina 175 while also directing image light 185 of retina 175 (i.e., the retinal image) along an image path to image sensor 110. Image light 185 is formed by the scattered reflection of illumination light 180 off of retina 175. In the illustrated embodiment, the optical relay system further includes beam splitter 150, which passes at least a portion of image light 185 to image sensor 110 while also directing display light 190 output from display 125 to eye 170. Beam splitter 150 may be implemented as a polarized beam splitter, a non-polarized beam splitter (e.g., 90% transmissive and 10% reflective, 50/50 beam splitter, etc.), a dichroic beam splitter, or otherwise. The optical relay system includes a number of lenses, such as lenses 135, 140, and 145, to focus the various light paths as needed. For example, lens 135 may include one or more lensing elements that collectively form an eyepiece that is displaced from the cornea of eye 170 by an eye relief 195 during operation. Lens 140 may include one or more lens elements for bringing image light 185 to a focus on image sensor 110. Lens 145 may include one or more lens elements for focusing display light 190. It should be appreciated that the optical relay system may be implemented with a number and variety of optical elements (e.g., lenses, reflective surfaces, diffractive surfaces, etc.).

The image sensor 110 may sense light in the visible spectrum and the infrared spectrum. The image sensor 110 may include separate visible light and infrared image sensors, or a single image sensor capable of sensing both visible and infrared light.

In one embodiment, display light 190 output from display 125 is a fixation target or other visual stimuli. The fixation target not only can aid with obtaining alignment between retinal imaging system 100 and eye 170 by providing visual feedback to the patient, but may also give the patient a fixation target upon which the patient can accommodate their vision. Display 125 may be implemented with a variety of technologies including a liquid crystal display (LCD), light emitting diodes (LEDs), various illuminated shapes (e.g., an illuminated cross or concentric circles), or otherwise.

Controller 115 is coupled to image sensor 110, display 125, dynamic illuminator 105, and alignment tracker 130 to choreograph their operation. The controller 115 may include logic that when executed by the controller 115 causes the controller 115 to control the image sensor 110, display 125, dynamic illuminator 105, and alignment tracker 130.

Controller 115 may include software/firmware logic executing on a microcontroller, hardware logic (e.g., application specific integrated circuit, field programmable gate array, etc.), or a combination of software and hardware logic. Although FIG. 1 illustrates controller 115 as a distinct functional element, the logical functions performed by controller 115 may be decentralized across a number of hardware elements. Controller 115 may further include input/output (I/O ports), communication systems, or otherwise. Controller 115 is coupled to user interface 120 to receive user input and provide user control over retinal imaging system 100. User interface 120 may include one or more buttons, dials, feedback displays, indicator lights, etc.

Image sensor 110 may be implemented using a variety of imaging technologies, such as complementary metal-oxide-semiconductor (CMOS) image sensors, charged-coupled device (CCD) image sensors, or otherwise. In one embodiment, image sensor 110 includes an onboard memory buffer or attached memory to store retinal images.

Alignment tracker 130 operates to track alignment between retinal imaging system 100 and eye 170, including a gaze direction 171 of the eye 170. The alignment tracker 130 may operate using a variety of different techniques to track the relative positions of eye 170 and the retinal imaging system 100 including pupil tracking, retina tracking, iris tracking, or otherwise. These various tracking techniques may be used by the retinal imaging system 100 to determine the relative position of the eye 170 to the retinal imaging system as well as the gaze direction 171 of the eye 170. In one embodiment, alignment tracker 130 is a gaze tracking camera that includes one or more infrared (IR) emitters to track eye 170 via IR light.

During operation, controller 115 operates dynamic illuminator 105 and image sensor 110 to capture one or more retinal images. Dynamic illuminator 105 is dynamic in that its illumination pattern is not static; but rather, is dynamically changed under the influence of controller 115 based upon the determined alignment with eye 170 (discussed in detail below). Illumination light 180 is directed through the pupil of eye 170 to illuminate retina 175. The scattered reflections from retina 175 are directed back along the image path through an aperture in inner baffle 155 to image sensor 110. Inner baffle 155 operates to block deleterious reflections and light scattering that would otherwise malign the retinal image while passing the image light itself through the central aperture defined by the inner baffle 155. The illumination patterns output by dynamic illuminator 105 are selected based upon the current alignment to reduce deleterious image artifacts. Image artifacts may arise from light scattering by the human lens within eye 170, reflections from the cornea/iris, or even direct specular reflections of illumination light 180 from retina 175. Direct specular reflections from retina 175 or the cornea/iris can create washed out regions in the retinal image. The dynamic changes in the illumination patterns output from dynamic illuminator 105 serve to direct these specular reflections off axis from the image path and therefore blocked by the inner baffle 155.

Figure 2A:
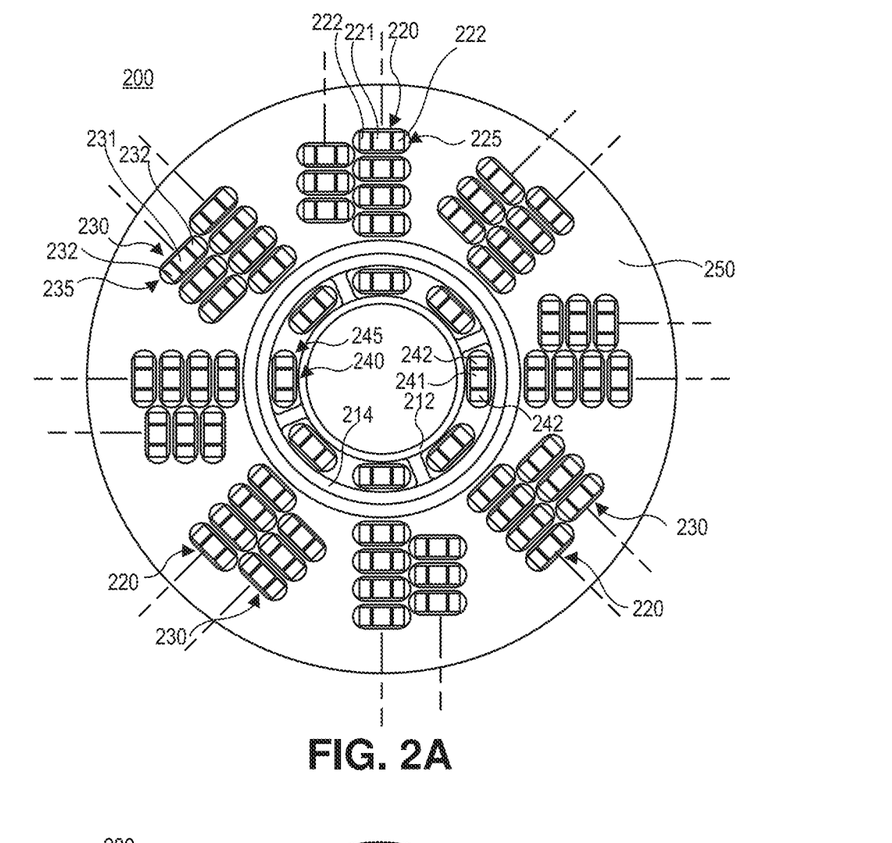
FIGS. 2A & 2B illustrate various views of a dynamic illuminator having primary illumination arrays and secondary illumination arrays extending parallel to one another, in accordance with an embodiment of the disclosure.
Figure 2B:
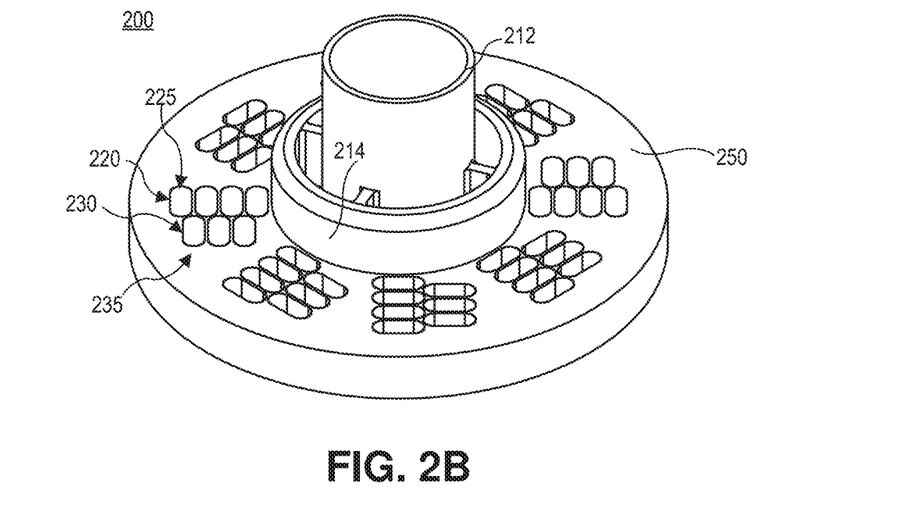

FIGS. 2A & 2B illustrate various views of a dynamic illuminator 200 having primary illumination arrays 220 and secondary illumination arrays 230 (only a portion are labeled) extending parallel to one another, in accordance with an embodiment of the disclosure. The dynamic illuminator 200 may be an example of the dynamic illuminator 105 illustrated in FIG. 1. As illustrated in FIG. 2A, the dynamic illuminator 200 may include a ring of inner light sources 240, primary illumination arrays 220, secondary illumination arrays 230, inner baffle 212, outer baffle 214, and body 250.

The ring of inner light sources 240, the primary illumination arrays 220, the secondary illumination arrays 230, the inner baffle 212, and the outer baffle 214 may be mounted on or otherwise connected to the body 250. In some embodiments, the ring of inner light sources 240, the primary illumination arrays 220, and the secondary illumination arrays 230 may be mounted to the body 250 in a single plane. In other embodiments, the ring of inner light sources 240, the primary illumination arrays 220, and the secondary illumination arrays 230 may be mounted to the body 250 in different planes or with individual LEDs in different planes (different distances from the eye 170).

The inner baffle 212 may define a central opening in the dynamic illuminator 200. The outer baffle 214 may be located between the ring of inner light sources 240 and the primary and secondary illumination arrays 220, 230. The ring of inner light sources 240, the primary illumination arrays 220, and the secondary illumination arrays 230 may be disposed on or in the body 250. In one embodiment, body 250 is a monolithic housing structure. In other embodiments, body 250 may be fabricated from multiple components that connect together. Body 250 may be fabricated from plastic, metal, or otherwise.

The inner baffle 212 and outer baffle 214 strategically cast shadows onto eye 170 to confine the divergence pattern of the illumination from the ring of inner light sources 240. When the eye is in perfect alignment, the shadows cast by the inner baffle 212 and outer baffle 214 will cast a shadow on the center of the corneal plane and lens of the eye 170 to reduce deleterious reflections at the cornea and lens.

The ring of inner light sources 240 may include several inner light sources 245. For example, as illustrated in FIG. 2A the ring of inner light sources 240 may include eight inner light sources 245. Other example embodiments may include 4 or more inner light sources 245. The inner light sources 245 may be arranged in a ring around the central opening defined by the inner baffle 212 with each inner light source 245 having the same radial distance from a center of the central opening. The inner light sources 245 may be evenly spaced around the central opening. Each inner light source 245 may include a visible light source 241 and a pair of infrared light sources 242 on either side of the visible light source 241. The illumination of the ring of inner light sources 240 including individual control of the individual visible light sources 241 and infrared light sources 242 may be controlled by the controller 115.

The primary illumination arrays 220 may be arranged around the central aperture, such that the primary illumination arrays 220 extends along radial axes from the central aperture outside of the ring of inner light sources 240. As illustrated in FIG. 2A, the dynamic illuminator 200 may include eight primary illumination arrays 220. Other embodiments with a different number of primary illumination arrays 220 are also possible. Each primary illumination array 220 may extend in a direction radially outward from the center of the central aperture and may be evenly spaced around the center of the central aperture. Each of the inner light sources 245 of the ring of inner light sources 240 may share a common polar angle as one of the radial axes of the primary illumination arrays 220.

Each primary illumination array 220 may consist of multiple primary light sources 225. The primary illumination array 220 may include four primary light sources 225. The primary illumination array 220 in other example embodiments may include a different number of primary light sources 225. Each primary light source 225 may include a visible light source 221 and a pair of infrared light sources 222 on either side of the visible light source 221. Each primary light source 225 may have a different radial distance from the center of the central aperture. The illumination of primary light sources 225 including individual control of the individual visible light sources 221 and infrared light sources 222 may be controlled by the controller 115.

Each secondary illumination array 230 may be arranged next to one of the primary illumination arrays 220 (or proximate primary illumination array 220) on the body 250. As illustrated in FIG. 2A, the dynamic illuminator 200 may include eight secondary illumination arrays 230. Other embodiments with a different number of secondary illumination arrays 230 are also possible. The secondary illumination arrays 230 may be disposed along secondary axes extending from the central aperture outside of the ring of inner light sources 240. The secondary axes of the secondary illumination arrays 230 are disposed angularly between adjacent ones of the primary illumination arrays 220. Restated, each secondary illumination array 230 may extend in a direction away from the central aperture and parallel to the proximate primary illumination array 220. Each secondary illumination array may extend away from the central aperture but not radially outward from the center of the central aperture. The secondary illumination array 230 may include three secondary light sources 235. In other example embodiments, the secondary illumination array 230 may include a different number of secondary light sources 235. Each of the secondary light sources 235 are offset from the primary light sources 225 to have a radial distance from a center of the central aperture different from that of each of the primary light sources in the proximate primary illumination arrays 220. Accordingly, secondary light sources 235 provide intermediate spacing between the adjacent primary light sources 225. This intermediate spacing has a smaller pitch than the physical size of primary light sources 225 would otherwise permit when organized in a straight line. As such, secondary light sources 235 provide increased granularity for selecting the location of illumination during retinal imaging.

Each secondary light source 235 may include a visible light source 231 and a pair of infrared light sources 232 on either side of the visible light source 231. Each secondary light source 235 in one of the secondary illumination arrays 230 may have a different radial distance from the center of the central aperture. The radial distance from the center aperture of each of the secondary light sources 235 may be between two of the radial distances between two of the primary light sources 235 of the proximate primary illumination array 220. Restated, each secondary light source 235 may have a different radial distance from the center of the central aperture than the primary light sources 225 in the proximate primary illumination array 220. The illumination of secondary light sources 235 including individual control of the individual visible light sources 231 and infrared light sources 232 may be controlled by the controller 115. Illumination light 180 may come from any of the visible light sources, 221, 231, 241 or a combination of the visible light sources 221, 231, 241. The visible light sources 221, 231, 241 may be white light LEDs. The infrared light sources 222, 232, 242 may be infrared LEDs.

FIG. 2B illustrates the dynamic illuminator 200 from a different point of view. As illustrated, the outer baffle 214 is shorter than the inner baffle 212. The primary and secondary light sources 225, 235 may be disposed in cavities in the body 250. These cavities also form light baffles for constraining the divergence pattern of each light source external to outer baffle 214.

Figure 3A:
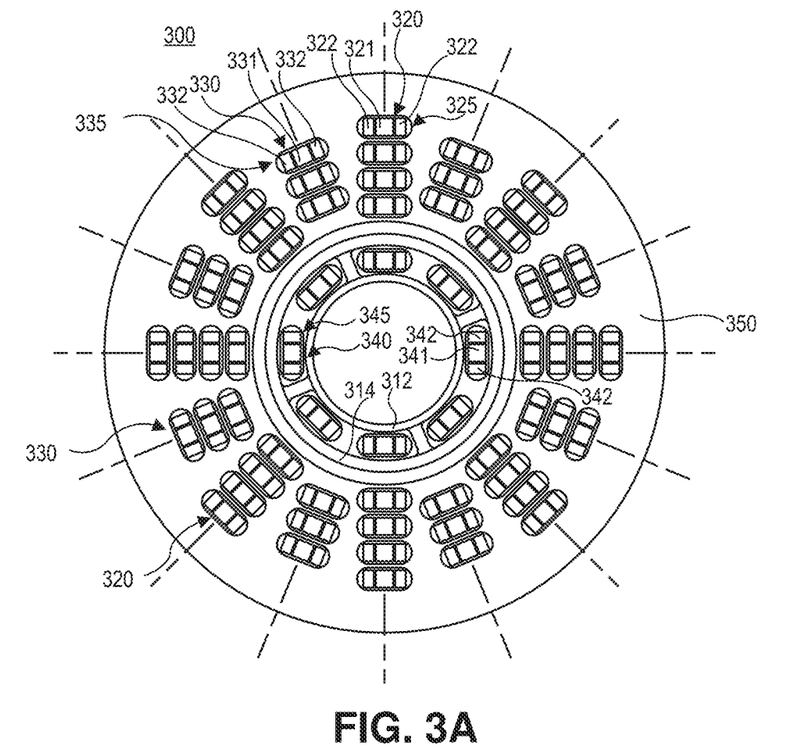
FIGS. 3A & 3B illustrate various views of a dynamic illuminator having primary illumination arrays and secondary illumination arrays extending radially from a center of a central aperture, in accordance with an embodiment of the disclosure.
Figure 3B:
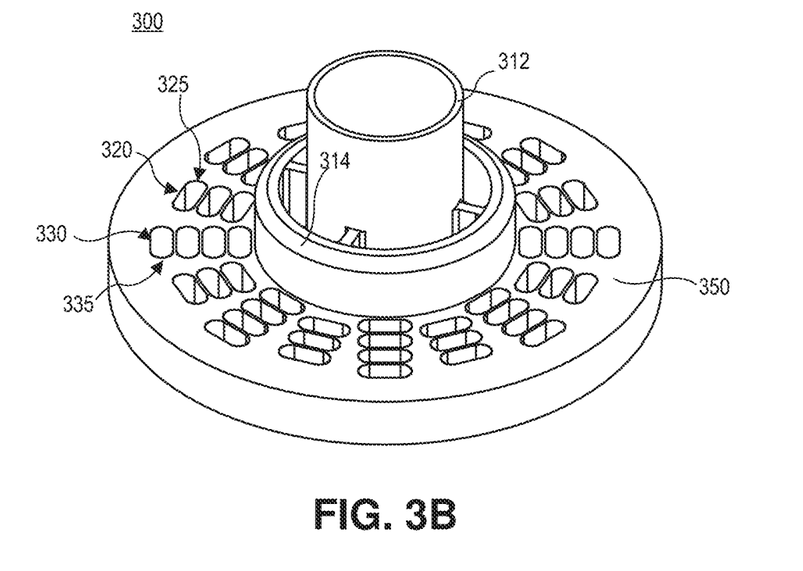

FIGS. 3A & 3B illustrate various views of a dynamic illuminator 300 having primary illumination arrays 320 and secondary illumination arrays 330 extending radially from a center of a central aperture, in accordance with an embodiment of the disclosure. The dynamic illuminator 300 may be another example of the dynamic illuminator 115 illustrated in FIG. 1. The dynamic illuminator 300 is similar to the dynamic illuminator 200 except that the secondary illumination arrays 330 extend radially from the center of the central aperture rather than parallel to one of the primary illumination arrays 320.

Accordingly, the body 350, inner baffle 312 and outer baffle 314 may be similar to the body 250, inner baffle 212, and outer baffle 214, respectively. The ring of inner light sources 340, inner light sources 345, visible light sources 341 and infrared light sources 342 may be similar to the ring of inner light sources 240, inner light sources 245, visible light sources 241 and infrared light sources 242, respectively. The primary illumination arrays 320, primary light sources 325, visible light sources 321 and infrared light sources 322 may be similar to the primary illumination arrays 220, primary light sources 225, visible light sources 221 and infrared light sources 222, respectively. The secondary illumination arrays 330, secondary light sources 335, visible light sources 331 and infrared light sources 332 may be similar to the secondary illumination arrays 230, secondary light sources 235, visible light sources 231 and infrared light sources 232, respectively, except for their location on the body 350.

The secondary illumination arrays 330 may be arranged to extend along secondary axes radially outward from the center of the central aperture. Each secondary illumination array 330 may be evenly spaced between two of the primary illumination arrays 320 (proximate primary illumination arrays 320). Restated, the primary illumination arrays 320 and the secondary illumination arrays 330 are angularly evenly spaced around the central aperture. Each secondary illumination array 330 may consist of multiple secondary light sources 335. Each secondary light source 335 may include a visible light source 331 and a pair of infrared light sources 332 on either side of the visible light source 331. Each secondary light source 335 in one of the secondary illumination arrays 320 may have a different radial distance from the center of the central aperture. The radial distance from the center aperture of each of the secondary light sources 335 may be between two of the radial distances of the primary light sources 335 of the proximate primary illumination arrays 320. Restated, each secondary light source 235 may have a different radial distance from the center of the central aperture than the primary light sources 325 in the proximate primary illumination arrays 320. The illumination of secondary light sources 335 including individual control of the individual visible light sources 331 and infrared light sources 332 may be controlled by the controller 115. Illumination light 180 may come from any of the visible light sources, 321, 331, 341 or a combination of the visible light sources 321, 331, 341.

Figure 4A:
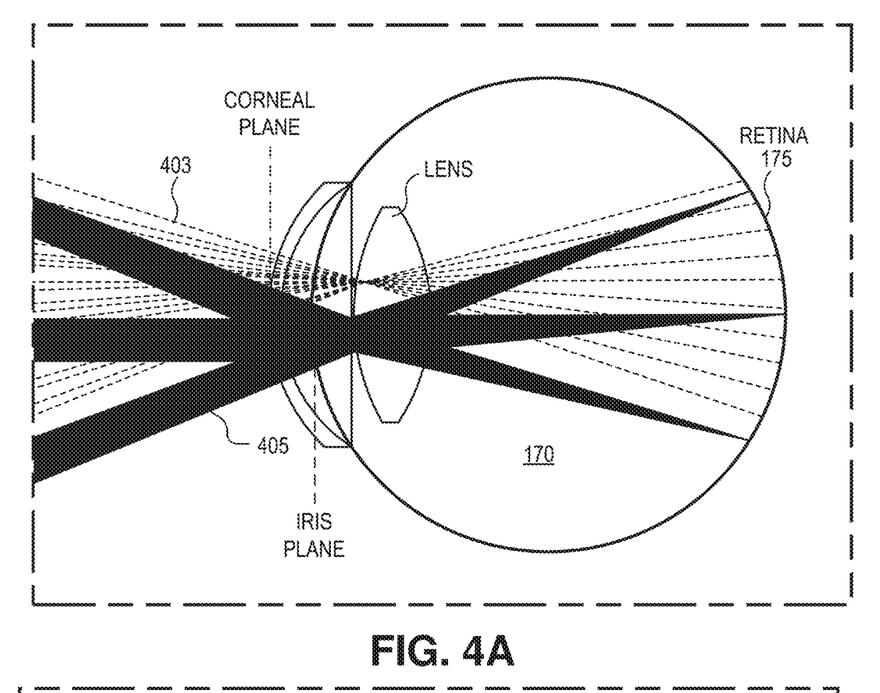
FIGS. 4A & 4B illustrate the illumination of an eye and the resulting incident light.
Figure 4B:
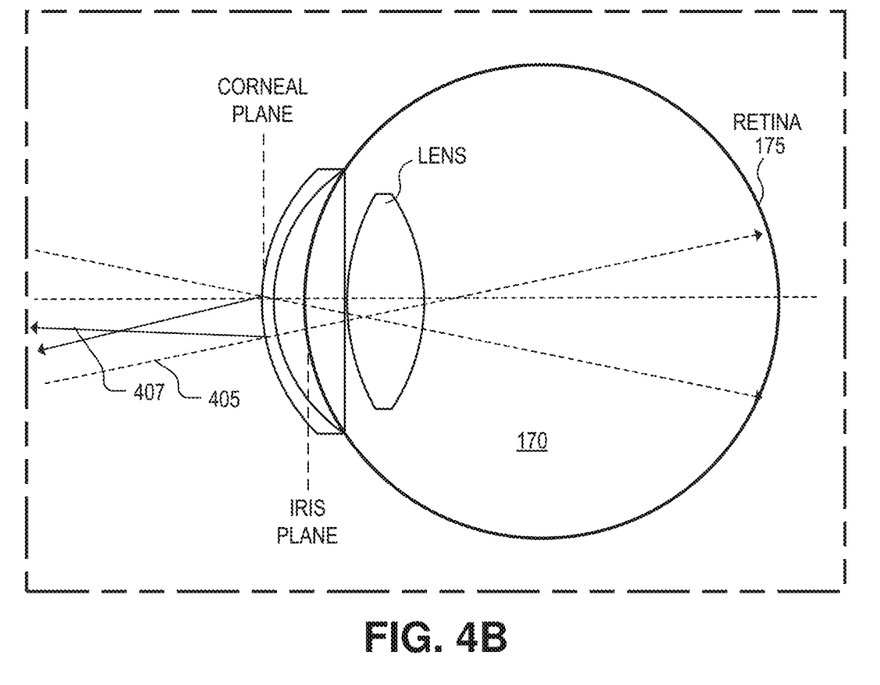

FIGS. 4A & 4B illustrate the illumination of an eye 170 and the resulting incident light. As illustrated in FIG. 4A, in order to illuminate the retina, the illumination light 405 passes through the corneal plane, iris plane, and lens. The image light 403 also passes through the lens, iris plane, and corneal plane as it leaves the eye 170. As the illumination light 405 passes through the corneal plane, iris plane, and lens, deleterious reflections may result. These deleterious reflections may cause portions of the image captured by the image sensor 110 to be washed out or otherwise unusable. Reflections off of the corneal plane may be of particular concern.

FIG. 4B shows how the illumination light 405 may cause a reflection 407 which may wash out a portion of the image from the image light 403 if the reflection 407 overlaps with the illumination light when received by the image sensor 110. The angle at which the illumination light 407 passes through the corneal plane determines whether the reflection 407 overlaps with the image light or not.

Figure 5A:
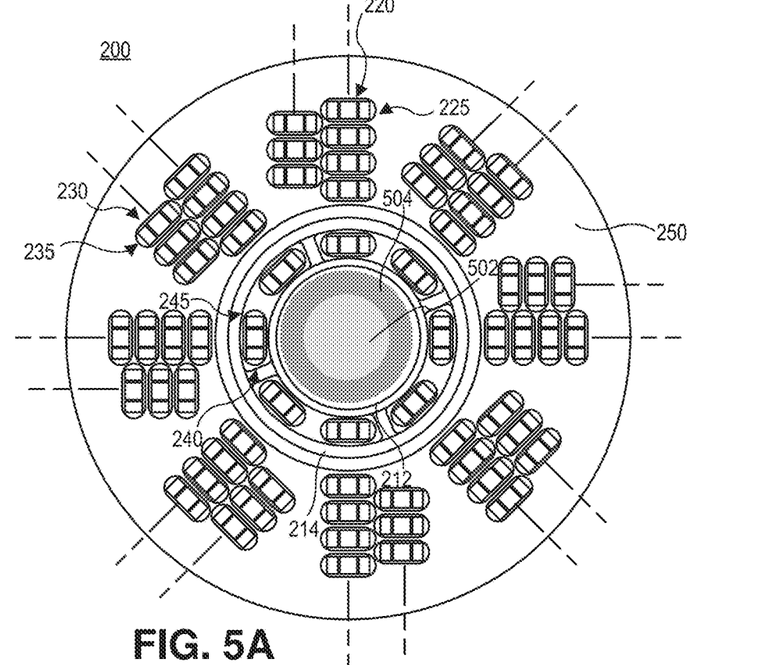
FIGS. 5A & 5B illustrate example areas of the dynamic illuminator which will adequately illuminate the retina of an eye of a user based on the positioning of the eye of the user and example areas which will cause image artifacts from corneal reflections based on the positioning of the eye of the user.
Figure 5B:
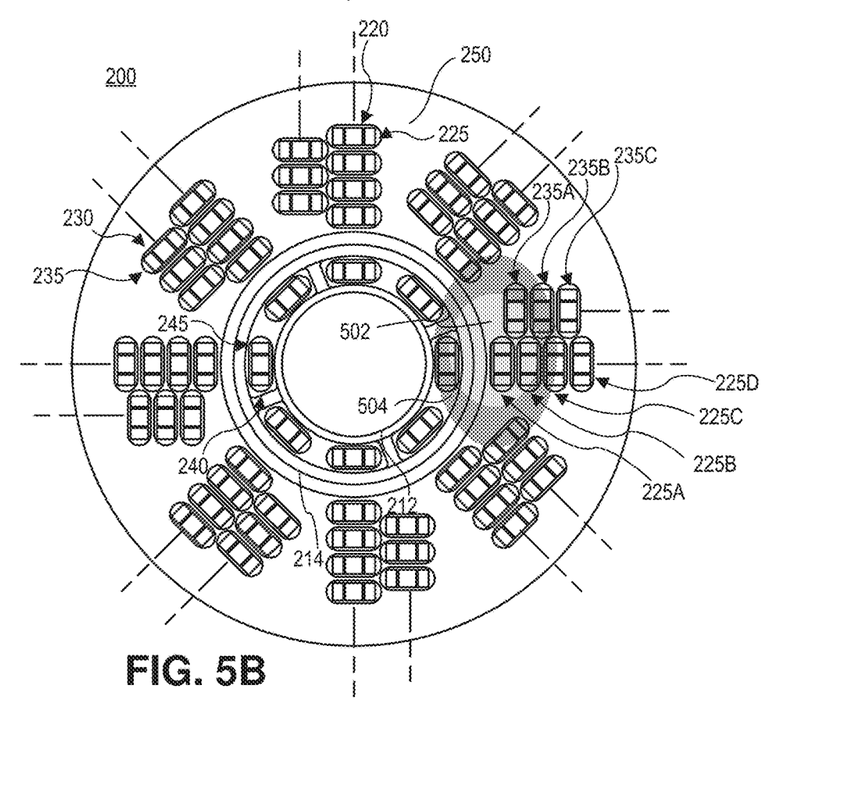

FIGS. 5A & 5B illustrate example areas of the dynamic illuminator 200 which will adequately illuminate the retina 175 of an eye of a user based on the positioning of the eye 170 of the user and example areas which will cause image artifacts from corneal reflections based on the positioning of the eye of the user. The dynamic illuminator 200 is used for example purposes. The description of the areas of the dynamic illuminator 200 applies equally to dynamic illuminator 300 or other example embodiments.

As stated above, the angle at which the illumination light 407 enters the corneal plane determines if the reflection 407 will overlap with the image light 403. The angle at which the illumination light 407 passes through the pupil will determine if the entire retina 175 is sufficiently illuminated for retina imaging. The alignment of the eye 170 with the retinal imaging system 100 will cause light emitted from a visible light source 221, 231, 241 at certain areas of the dynamic illuminator 105 to illuminate the retina 175 to different degrees. For example, a visible light source 221, 231, 241 in the full illumination area 504 will fully illuminate the retina 175, while visible light source 221, 231, 241 in other areas will only partially illuminate the retina 175. Accordingly, it is possible to completely illuminate the retina 175 with only one visible light source 221, 231, 241. If the eye 170 moves, the full illumination area 504 will move in a corresponding manner and different visible light sources 221, 231, 241 could fully illuminate the retina 175.

The alignment of the eye 170 with the retinal imaging system 100 will cause light emitted from a visible light source 221, 231, 241 at certain areas of the dynamic illuminator 105 to cause reflections which wash out portions of the retina 175. These reflections are examples of deleterious image artifacts. For example, a visible light source 221, 231, 241 in the reflection area 502 may cause a reflection off the corneal plane of the eye 170 that overlaps with the image light 403. The size and shape of the full illumination area 504 and the reflection area 502 are determined by the shape and size of the eye 170 and the alignment of the eye 170 with the retinal imaging system 100.

FIG. 5A illustrates the case where the eye 170 is in perfect alignment with the retinal imaging system 100. In this case, the full illumination area 504 and the reflection area 502 are in the central aperture and no light source may fully illuminate the retina 175. However, a combination of the light from all of the visible light sources 241 in the ring of inner light sources 240 can together illuminate the retina 175. In similar cases of near perfect alignment (minor misalignment), the visible light sources 241 in the ring of visible light sources 240 can together illuminate the retina 175 without a reflection in the image captured by the image sensor 110, as long as the reflection area 502 does not overlap with any of the visible light sources 241. The inner baffle 212 and the outer baffle 214 causes the reflection area 502 to be smaller for the ring of inner light sources 240 than for the primary and secondary light sources 225, 235.

As illustrated in FIG. 5A, the closer the eye 170 is to perfect alignment the closer the full illumination area 504 and the reflection area 502 are to being concentric circles in the center of the dynamic illuminator 105 (aligning with the center of the central aperture). As alignment shifts away from perfect, the shape and location of the full illumination area 504 and the reflection area 502 changes.

Misalignment can lead to deleterious corneal reflections, refractive scattering from the crystalline lens, and occlusion of the imaging aperture. Conventional imaging systems have relatively small eyeboxes, which require precise alignment to avoid image artifacts from entering the image path. The dynamic illuminator 200, 300 combines two different illumination architectures—one when the eye is roughly aligned with the optical axis or gaze direction of the eye (ring of inner light sources 240, 340) and one when the eye is offset from the optical axis or gaze direction of the eye (primary and secondary illumination arrays 220, 320, 230, 330). By dynamically switching between these two illumination architectures, the eyebox of the retinal imaging system described herein may be expanded by 2× or more over conventional ring illuminators.

As the eye 170 shifts in a transverse direction relative to the retinal imaging system 100, the full illumination area 504 and the reflection area 502 may shift in a transverse direction. Also, the relative movement of the full illumination area 504 and the reflection area 502 may be different such that the full illumination area 504 shifts more than the reflection area 502. This type of misalignment may be corrected manually by adjusting the retinal imaging system 100 or by the illumination processes described below.

As illustrated in FIG. 5B, in the case where the eye 170 is out of position angularly (such that the pupil is not directed exactly at the central aperture), the shape of the full illumination area 504 and the reflection area 502 may move away from the center of the central aperture and elongate in a direction perpendicular to the direction toward the center of the central aperture. This type of misalignment can be difficult to adjust for by manually adjusting the retinal imaging system 100 because a person's eye moves constantly even when the person is trying to keep the eye focused on a single location.

The primary and secondary image arrays 220, 230 may be used to compensate for either type of misalignment (transverse or angular). The primary and secondary light sources 225, 235 are arranged in order to have one visible light source 221, 231 in the full illumination area 504 and not in the reflection area 502 for any moderate misalignment caused by the ordinary movements of the eye 170 with a pupil size of about four to ten millimeters. The area of the full illumination area 504 outside of the reflection area 502 may be relatively small compared to the practical limits on the distances between LEDs operating at the required power levels. Further, because, the illumination area extends in a direction perpendicular to the direction to the center of the central aperture, the radial distance to the center of the central aperture becomes more important than the radial angle of the light source. Thus, the first light sources 225 and second light sources 235 have different radial distances to the center of the central aperture so that at least one of the visible light sources 221, 231 is within the full illumination area 504 and outside of the reflection area 502.

FIG. 5B includes first, second, third, and fourth primary light sources 225A, 225B, 225C, 225D, and first, second, and third secondary light sources 235A, 235B, 235C. As is illustrated in FIG. 5B, the first and second primary light sources 225A, 225B are within the reflection area 502. The third and fourth primary light sources 225C, 225D are outside of the full illumination area and would only provide partial illumination of the retina 175. However, second secondary light source 235B is in the full illumination area 504 and not in the reflection area 502. Accordingly, it may be possible to achieve adequate illumination of the retina 175 without any corneal reflection from the second secondary light source 235B. Thus, a moderate misalignment may be compensated for by using the second secondary light source 235B.

Figure 6A:
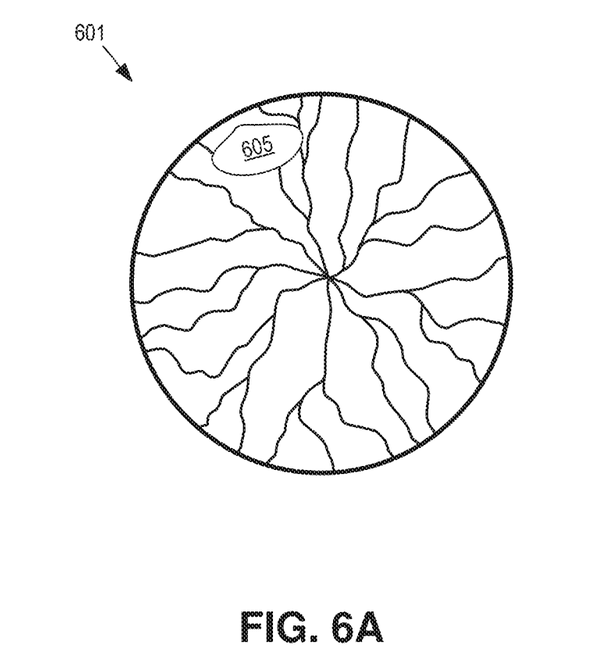
FIGS. 6A & 6B illustrate retinal images including image artifacts, in accordance with an embodiment of the disclosure.
Figure 6B:
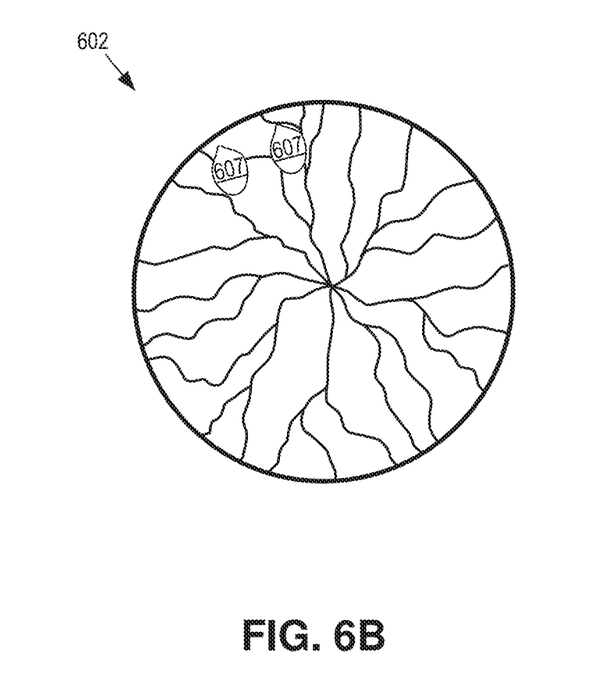

FIGS. 6A & 6B illustrate retinal images including image artifacts, in accordance with an embodiment of the disclosure. FIG. 6A illustrates an example retinal image 601 taken in visible light with one of the visible light sources 221, 231, 241 with an image artifact 605. The image artifact 605 may arise when misalignment between the retinal imaging system and the eye permit stray light and deleterious reflections from the visible light sources 221, 231, 241 to enter the image path and ultimately are captured by the image sensor with the retinal image light.

FIG. 6B illustrates an example infrared retinal image 602 taken in infrared light with a pair of the infrared light sources 222, 232, 242 from the same light source as the visible light source 221, 231, 241 from FIG. 6A with image artifacts 607. As can be seen, the artifacts 607 in the infrared retinal image 602 are in roughly the same area of the infrared image 602 as the artifact 605 in the retinal image 601. Accordingly, the location of artifacts 607 in an infrared retina image 602 is indicative of where an artifact 605 may appear in a retinal image 601 in visible light (between the artifacts 607 in the infrared retinal image 602).

Infrared is not visible to the human eye. Accordingly, the eye does not react to infrared in the same way as visible light (for example, closing of eyelids, restricting pupil size, or looking away). Accordingly, taking retina images in infrared light combined with rapid image processing may be used to determine if a visible light source 221, 231, 241, 321, 331, 341 may be used to image the retina 175 in visible light with adequate illumination and without deleterious image artifacts.

Figure 7:
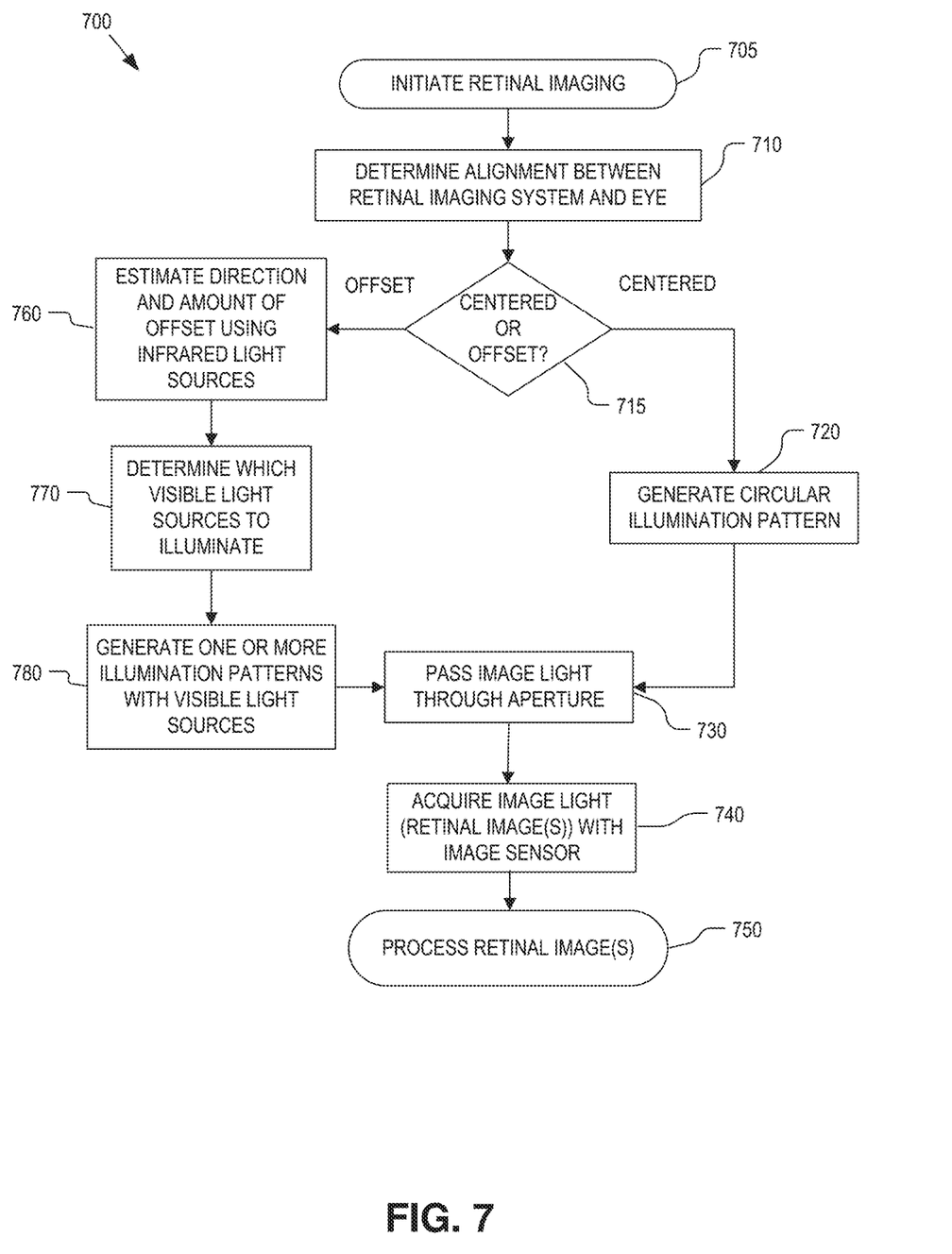
FIG. 7 is a flow chart illustrating operation of the retinal imaging system, in accordance with an embodiment of the disclosure.

FIG. 7 is a flow chart illustrating a process 700 for operation of retinal imaging system 100, in accordance with an embodiment of the disclosure. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel. The process 700 may be controlled by the controller 115.

In a process block 705, the retinal imaging process is initiated. Initiation may include the user selecting a power button from user interface 120. In a process block 710, alignment tracker 130 commences tracking and determining the alignment between retinal camera system 100 and eye 170. In particular, tracking may be determined as a relative measurement between eyepiece lens 135 and the pupil, iris, or retina of eye 170. A variety of different alignment tracking techniques may be implemented including pupil tracking, iris tracking, retinal tracking, trial and error, etc. The alignment tracking is used to determine which of the illumination schemes should be used for illuminating retina 175 during image acquisition. The transition between these illumination schemes may be abrupt or a smooth fading therebetween as the relative alignment wanders between a central alignment and an offset alignment.

In decision block 715, if retinal camera system 100 is determined to be centrally aligned with the gaze direction 171 (e.g., optical axis of eye 170) within a defined threshold, then process 700 continues to a process block 720. The alignment may be determined to be centrally aligned by using the alignment tracker to determine the general alignment of the eye 170 and/or capturing an infrared image using the infrared light sources 242, 342 to illuminate the retina 175. If an image analysis of the image shows that the retina 175 is fully illuminated without any deleterious inclusions then the controller 115 may determine that the retinal camera system 100 is centrally aligned with the gaze direction 171.

In process block 720, dynamic illuminator 105 is operated by controller 115 to generate a circular illumination pattern for illuminating retina 175 through the pupil of eye 170 by turning on all of the inner light sources 245, 345 of the ring of inner light sources 240, 340.

The emission divergence patterns of visible light sources 241, 341 are constrained and controlled by inner and outer baffles 212, 312, 214, 314 and a shadow cast by inner baffle 212, 312. Inner baffle 212, 312 serves to block the portion of the illumination light output from visible light sources 241, 341 that would cause deleterious scattering in eye 170. Inner baffle 305 strategically casts an illumination shadow onto eye structures that cause reflections (perpendicular portion of corneal plane and lens) to reduce image artifacts captured by image sensor 110.

In process block 730, the retinal image passes through the central aperture defined by the inner baffle 212, 312 while the inner baffle 212, 312 further blocks deleterious reflections and other stray refractions. Then, in the process block 740, the image sensor 110 acquires image light 185 forming the retinal image. The operations of process blocks 720, 730, and 740 may be performed several times. Or restated, several retinal images may be captured in quick succession. Generally 6 to 20 images can be captured before the eye 170 reacts to the bright flash of the visible light sources. Accordingly, the operations of process blocks 720, 730, and 740 may be performed up to about 20 times in a row.

In process block 750, the controller may process the retinal image (or retinal images) to ensure adequate image quality. For example, image processing may be done to check for adequate illumination of the retina and for deleterious image artifacts. During image processing the retinal images may be combined (e.g. image stacking) to exclude deleterious image inclusions from the retinal images.

Returning to decision block 715, if retinal camera system 100 is determined to be offset from the gaze direction 171 by a defined threshold (a moderate misalignment), then process 700 continues to process blocks 760. In process blocks 760, the direction and amount of offset is estimated using the infrared light sources 222, 232, 322, 332. The direction and amount of offset may be estimated in several different ways.

As a first example, the alignment tracker 130 may detect the direction of the offset of the gaze of the user. The infrared light sources 222, 322, 232, 332 of the primary and secondary light sources 225, 325, 235, 335 in the detected direction of offset may then be used to capture infrared retinal images to determine which of the primary and secondary light sources 225, 325, 235, 335 may provide adequate illumination of the retina 175 without deleterious image artifacts in the visual spectrum.

As a second example, the infrared retinal image taken in process block 710 may be used to determine the direction of the offset by analyzing the illumination pattern of the retinal image. Then, the infrared light sources 222, 322, 232, 332 of the primary and secondary light sources 225, 325, 235, 335 in the determined direction of offset may then be used to capture infrared retinal images to determine which of the primary and secondary light sources 225, 325, 235, 335 may provide adequate illumination of the retina 175 without deleterious image artifacts in the visual spectrum.

As a third example, a method of guess and check using the infrared light sources 222, 322, 232, 332 of the primary and secondary light sources 225, 325, 235, 335 may be used to estimate the direction and amount of offset.

At process block 770, the captured infrared retinal images may be processed by the controller 115 in order to determine which visible light sources 221, 321, 231, 331 of the primary and secondary light sources 225, 325, 235, 335, may provide adequate illumination of the retina 175 in the visual spectrum without deleterious image artifacts. Some differences in illumination and image artifacts will exist between retinal images captured using the infrared light sources 222, 322, 232, 332 and the visible light sources 221, 321, 231, 331 even for the same one of the primary and secondary light sources 225, 325, 235, 335. Also, as stated above, the human eye constantly moves. Further, as stated above, generally 6 to 20 retinal images may be captured in visible light before the eye reacts to visible light. Accordingly, the controller 115 may determine to first capture a retinal image using visible light illumination from one of the primary and secondary light sources 225, 325, 235, 335. The controller 115 may also determine which other primary and secondary light sources 225, 325, 235, 335 to use to capture subsequent images in rapid succession. For example, the controller 115 may determine to capture retinal images from each of the primary light sources 225, 325 in one of the primary illumination arrays 220, 320 and each of the secondary light sources 235, 335 of one of the secondary illumination arrays 230, 330. The controller 115 may also determine to capture multiple retinal images using one of the primary and secondary light sources 225, 325, 235, 335.

Alternatively or additionally, the controller 115 may determine to capture retinal images using multiple of the primary and secondary light sources 225, 325, 235, 335. For example, multiple of the primary and secondary light sources 225, 325, 235, 335 in different primary and secondary illumination arrays 220, 320, 230, 330 may be used to compensate for inadequate illumination of the retina from a single primary or secondary light source 225, 325, 235, 335. Restated, the controller 115 may determine to use a combination of primary and secondary light sources 225, 325, 235, 335 to illuminate the retina 175 while capturing a retinal image.

In process block 780 the dynamic illuminator 105 is operated by controller 115 to generate an illumination pattern (using one or more of the primary and secondary light sources 225, 325, 235, 335) for illuminating retina 175 through the pupil of eye 170. The image light then passes through the central aperture, at process block 730. At process block 740, the image sensor 110 is also controlled by the controller 115 to capture the retinal image(s). Multiple retinal images may be captured in quick succession.

At process block 750, the controller 115 may process the retinal image(s) to determine if any of the retinal images have adequate illumination of the retina without deleterious image artifacts. The controller 115 may also combine retinal images together to remove deleterious image artifacts or fill in areas of the retinal image with inadequate illumination.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A dynamic illuminator comprising:
a central aperture;
a ring of inner light sources arranged around the central aperture;
a plurality of primary illumination arrays extending along radial axes from the central aperture outside of the ring of inner light sources, wherein the primary illumination arrays each includes a plurality of primary light sources; and
a plurality of secondary illumination arrays disposed along secondary axes extending from the central aperture outside of the ring of inner light sources, wherein the secondary illumination arrays each includes a plurality of secondary light sources, wherein the secondary axes of the secondary illumination arrays are disposed angularly between adjacent ones of the primary illumination arrays, and wherein each of the secondary light sources are offset from the primary light sources to have a radial distance from a center of the central aperture different from that of each of the primary light sources in the adjacent ones of the primary illumination arrays.

2. The dynamic illuminator of claim 1, wherein each of the primary light sources, each of the secondary light sources, and each of the inner light sources includes a visible light source and an infrared light source.

3. The dynamic illuminator of claim 1, further comprising:
an inner baffle defining the central aperture and disposed radially interior to the ring of inner light sources.

4. The dynamic illuminator of claim 3, further comprising:
an outer baffle disposed radially exterior to the ring of inner light sources and further disposed between the ring of inner light sources and the primary and secondary illumination arrays, wherein the outer baffle is shorter than the inner baffle.

5. The dynamic illuminator of claim 1, wherein each of the secondary axes is parallel to but offset from one of the radial axes of the primary illumination arrays such that the secondary axes do not run radially from the center of the central aperture.

6. The dynamic illuminator of claim 1, wherein the secondary axes each extend radially from the center of the central aperture.

7. The dynamic illuminator of claim 6, wherein the primary illumination arrays and the secondary illumination arrays are angularly evenly spaced around the central aperture.

8. The dynamic illuminator of claim 1, wherein each of the inner light sources of the ring of inner light sources shares a common polar angle with one of the radial axes of the primary illumination arrays.

9. The dynamic illuminator of claim 1, wherein the ring of inner light sources includes eight inner light sources, the primary illumination arrays include eight primary illumination arrays, and the secondary illumination arrays include eight secondary illumination arrays.

10. A retinal imaging system, comprising:
an image sensor adapted to acquire a retinal image;
a dynamic illuminator including:
a central aperture through which the retinal image is acquired;
a plurality of primary illumination arrays extending along radial axes from the central aperture, wherein the primary illumination arrays each includes a plurality of primary light sources; and
a plurality of secondary illumination arrays disposed along secondary axes extending from the central aperture, wherein the secondary illumination arrays each includes a plurality of secondary light sources each offset from the primary light sources to have a radial distance from a center of the central aperture different from that of each of the primary light sources in an adjacent one of the primary illumination arrays; and
a controller coupled to the image sensor and the dynamic illuminator, the controller including logic that when executed by the controller causes the retinal imaging system to perform operations including:
determining an alignment between the retinal imaging system and an eye;
generating an illumination pattern output from the dynamic illuminator based upon the alignment; and
acquiring the retinal image with the image sensor while illuminating the eye with the illumination pattern.

11. The retinal imaging system of claim 10, wherein the dynamic illuminator further comprises:
a ring of inner light sources arranged around the central aperture.

12. The retinal imaging system of claim 11,
wherein the plurality of primary illumination arrays extend along the radial axes from the central aperture outside of the ring of inner light sources,
wherein the plurality of secondary illumination arrays disposed along the secondary axes extending from the central aperture outside of the ring of inner light sources, and
wherein the secondary axes of the secondary illumination arrays are disposed angularly between adjacent ones of the primary illumination arrays.

13. The retinal imaging system of claim 11, wherein the controller includes further logic that when executed by the controller causes the retinal imaging system to perform additional operations including:
generating the illumination pattern with the ring of inner light sources to illuminate the eye while acquiring the retinal image when the alignment is determined to be centered within a threshold; and
generating the illumination pattern with at least one of the primary or secondary illumination arrays to illuminate the eye while acquiring the retinal image when the alignment is determined to be off-center.

14. The retinal imaging system of claim 13, wherein the illumination pattern comprises a circular illumination pattern when the alignment is determined to be centered within the threshold.

15. The retinal imaging system of claim 11, wherein the dynamic illuminator further comprises:
an inner baffle defining the central aperture and disposed radially interior to the ring of inner light sources.

16. The retinal imaging system of claim 15, wherein the dynamic illuminator further comprises:
an outer baffle disposed radially exterior to the ring of inner light sources and further disposed between the ring of inner light sources and the primary and secondary illumination arrays, wherein the outer baffle is shorter than the inner baffle.

17. The retinal imaging system of claim 10, wherein the primary light sources and the secondary light sources each include an infrared light source and a visible light source.

18. The retinal imaging system of claim 17, wherein the controller includes further logic that when executed by the controller causes the retinal imaging system to perform further operations comprising:
generating an initial illumination pattern with one or more of the infrared light sources of the primary or secondary light sources based upon the alignment;
capturing an infrared retinal image; and
analyzing the infrared retinal image to determine whether the illumination pattern should be adjusted prior to capturing the retinal image with visible illumination.

19. The retinal imaging system of claim 10, wherein each of the secondary axes is parallel to but offset from one of the radial axes of the primary illumination arrays such that the secondary axes do not run radially from the center of the central aperture.

20. The retinal imaging system of claim 10, wherein the secondary axes each extend radially from the center of the central aperture.

* * * * *